(12) United States Patent
Liu et al.

(10) Patent No.: US 8,269,036 B2
(45) Date of Patent: Sep. 18, 2012

(54) PROCESSES FOR PRODUCING AN OXALATE BY COUPLING OF CO

(75) Inventors: Juntao Liu, Shanghai (CN); Zhiyan Zhu, Shanghai (CN); Wanmin Wang, Shanghai (CN); Lei Li, Shanghai (CN)

(73) Assignees: China Petroleum & Chemical Corporation, Beijing (CN); Shanghai Research Institute of Petrochemical Technology Sinopec, Shanghai (CN)

( * ) Notice: Subject to any disclaimer, the term of this patent is extended or adjusted under 35 U.S.C. 154(b) by 342 days.

(21) Appl. No.: 12/642,590

(22) Filed: Dec. 18, 2009

(65) Prior Publication Data

US 2010/0160671 A1 Jun. 24, 2010

(30) Foreign Application Priority Data

Dec. 18, 2008 (CN) .......................... 2008 1 0044140
Dec. 18, 2008 (CN) .......................... 2008 1 0044142

(51) Int. Cl.
*C07C 67/36* (2006.01)

(52) U.S. Cl. ....................................................... 560/204
(58) Field of Classification Search ........................ None
See application file for complete search history.

(56) References Cited

U.S. PATENT DOCUMENTS 4,467,109 A * 8/1984 Tahara et al. ................. 560/193

FOREIGN PATENT DOCUMENTS

| CN | 1148589 | 4/1997 |
| CN | 101143821 | 3/2008 |

* cited by examiner

*Primary Examiner* — Sudhakar Katakam
(74) *Attorney, Agent, or Firm* — Finnegan, Henderson, Farabow, Garrett & Dunner, LLP

(57) ABSTRACT

Provided are processes for producing an oxalate by coupling of CO in the presence of a nitrite, wherein two or more reaction zones in series are used, and at least a portion of the oxalate as reaction product is separated between the reaction zones, and/or the nitrite is fed stagewise. The processes described herein can effectively enhance the selectivity to the oxalate and the single-pass conversion of the feedstock.

20 Claims, No Drawings

PROCESSES FOR PRODUCING AN OXALATE BY COUPLING OF CO

The present application claims the benefit of Application Nos. CN200810044142.2 filed on Dec. 18, 2008, and CN200810044140.3 filed on Dec. 18, 2008.

Provided is a process for producing an oxalate by coupling of CO, for example, a process for producing dimethyl oxalate or diethyl oxalate by coupling of CO in the presence of methyl nitrite or ethyl nitrite.

Oxalates are important organic chemical feedstock, and are used widely in fine chemicals industry to produce various dyes, medicines, important solvents, extractants, and various intermediates. Furthermore, oxalates as monomers of degradable, environment friendly engineering plastics are drawing more and more attention. Oxalates can also be used, for example, in the production of oxalic acid via hydrolysis under atmospheric pressure, in the production of oxamide via ammonolysis under atmospheric pressure, and in the production of ethylene glycol via hydrogenation under lower pressure.

Traditionally, an oxalate could be prepared by esterification reaction between oxalic acid and an alcohol. This preparation route could result in high production cost, large energy consumption, serious pollution, and unreasonable feedstock use. For many years, a low cost, environment friendly process has been sought. In the 1960's, it was found that an dialkyl oxalate could be synthesized directly from CO, an alcohol, and oxygen by oxidative carbonylation.

The processes for synthesis of oxalates by oxidative coupling of carbon monoxide can be classified into liquid phase processes and gas phase processes. Liquid phase processes for oxidatively coupling carbon monoxide to synthesize an oxalate generally are conducted under higher pressure. Furthermore, the liquid phase system may erode the equipment, and it might be easy for catalysts to be entrained. In contrast, the process for gas-phase catalytically synthesizing an oxalate, for example, employs a reaction pressure of 0.5 MP and a reaction temperature of 80° C. to 150° C.

Provided is a process for producing an oxalate by coupling of CO, comprising a) feeding a nitrite and CO as feedstock to a first reaction zone to contact them with a first palladium-containing catalyst, to form a first reaction effluent containing unreacted nitrite, CO and oxalate product;

b) passing the first reaction effluent into a gas-liquid separator to conduct gas-liquid separation, to obtain a liquid product stream and a gas mixture stream;

c) feeding the liquid product stream obtained from b) to a separation unit, to obtain a first portion of the oxalate product;

d) feeding the gas mixture stream obtained from b) to a second reaction zone to contact it with a second palladium-containing catalyst, to form a second reaction effluent containing the oxalate; and e) feeding the second reaction effluent to the separation unit, to obtain a second portion of the oxalate product, wherein the molar ratio of CO to nitrite in the feedstock fed to the first reaction zone ranges, for example, from 1:1 to 5:1.

Also provided is a process for producing an oxalate by coupling of CO, comprising a) feeding a first nitrite stream and CO feedstock to a first reaction zone to contact them with a first palladium-containing catalyst, to form a first reaction effluent containing the oxalate;

b) optionally, passing the first reaction effluent into a gas-liquid separator to conduct gas-liquid separation, to obtain a gas stream and a liquid product stream, with the liquid product stream being passed into a separation unit to separate the oxalate product;

c) feeding the first reaction effluent or the gas stream obtained from b) together with a second nitrite stream to a second reaction zone to contact them with a second palladium-containing catalyst, to form a second reaction effluent containing the oxalate; and d) passing the second reaction effluent into a separation unit to separate the oxalate product, wherein the molar ratio of the nitrite in the first nitrite stream to the nitrite in the second nitrite stream ranges, for example, from 0.1:1 to 10:1, and wherein the molar ratio of the CO to the total nitrite in the first nitrite stream and the second nitrite stream ranges, for example, from 1:1 to 5:1.

In some embodiments, a process for producing an oxalate by coupling of CO (referred to as the first process hereinafter), comprises a) feeding a nitrite and CO as feedstock to a first reaction zone to contact them with a first palladium-containing catalyst, to form a first reaction effluent containing unreacted nitrite, CO and oxalate product;

b) passing the first reaction effluent into a gas-liquid separator to conduct gas-liquid separation, to obtain a liquid product stream and a gas mixture stream;

c) feeding the liquid product stream obtained from b) to a separation unit, to obtain a first portion of the oxalate product;

d) feeding the gas mixture stream obtained from b) to a second reaction zone to contact it with a second palladium-containing catalyst, to form a second reaction effluent containing the oxalate; and e) feeding the second reaction effluent to the separation unit, to obtain a second portion of the oxalate product, wherein the molar ratio of the CO to the nitrite in the feedstock fed to the first reaction zone ranges, for example, from 1:1 to 5:1, such as from 1:1 to 3:1.

In some embodiments of the first process, for example, in the case where the second reaction effluent still contains a relatively large quantity of unreacted CO and nitrite, a CO and nitrite-containing gas stream separated from the second reaction effluent is fed to a third reaction zone to contact with a third palladium-containing catalyst, to form a third reaction effluent containing the oxalate, from which a third portion of the oxalate product is separated.

In some embodiments of the first process, the first reaction zone is operated at a reaction temperature ranging from 60 to 130° C., such as from 70 to 120° C. In some embodiments of the first process, the first reaction zone is operated at a reaction contacting time ranging from 0.5 to 6 seconds, such as from 0.7 to 5 seconds. In some embodiments of the first process, the first reaction zone is operated at a reaction pressure ranging from 0.05 to 1.5 MPa (absolute, the same below), such as from 0.08 to 1.0 MPa. In some embodiments of the first process, the first reaction zone is operated under the following conditions: a reaction temperature ranging from 60 to 130° C., such as from 70 to 120° C.; a reaction contacting time ranging from 0.5 to 6 seconds, such as from 0.7 to 5 seconds; a reaction pressure ranging from 0.05 to 1.5 MPa (absolute, the same below), such as from 0.08 to 1.0 MPa.

In some embodiments of the first process, the second reaction zone is operated at a reaction temperature ranging from 70 to 150° C., such as from 80 to 140° C. In some embodiments of the first process, the second reaction zone is operated at a reaction contacting time ranging from 0.5 to 6 seconds, such as from 0.7 to 5 seconds. In some embodiments of the first process, the second reaction zone is operated at a reaction pressure ranging from 0.05 to 1.5 MPa, such as from 0.08 to 1.0 MPa. In some embodiments of the first process, the second reaction zone is operated under the following conditions: a reaction temperature ranging from 70 to 150° C., such as from 80 to 140° C.; a reaction contacting time ranging from 0.5 to 6 seconds, such as from 0.7 to 5 seconds; a reaction pressure ranging from 0.05 to 1.5 MPa, such as from 0.08 to 1.0 MPa. If a third reaction zone is used, the third reaction zone is operated under conditions similar to those as described for the second reaction zone.

The palladium-containing catalyst used in the first reaction zone, the second reaction zone or the optional third reaction zone may be any palladium-containing catalysts useful in the production of an oxalate by coupling of CO known in the art. The palladium-containing catalysts used may be the same or different.

In general, the palladium-containing catalysts used comprise at least one carrier chosen from silica, alumina and molecular sieves. In some embodiments, the palladium-containing catalysts described herein comprise alumina as the carrier. Examples of molecular sieves, which may be used as the catalyst carrier, include ZSM-5, mordenite, MCM-22, and β zeolite. The catalysts comprise palladium as active component in an amount ranging, for example, from 0.1 to 5 wt %, such as from 0.2 to 3 wt %, based on the weight of the carrier. The catalysts may further comprise an auxiliary active component, e.g. zirconium.

The catalysts may be prepared by a process known in the art. For example, a palladium-containing catalyst may be prepared by a process comprising: dissolving an amount of a water-soluble palladium salt, e.g., palladium nitrate, in water, and adjusting the solution with an acid, e.g., nitric acid or hydrochloric acid, to a pH value ranging, for example, from 3 to 6; after suitably heating the solution, impregnating a support, e.g., alumina, with the solution; drying the impregnated support and calcining it in air, to obtain the palladium-containing catalyst.

The nitrites used in the first process include, for example, methyl nitrite and ethyl nitrite. NO separated from the second reaction effluent or the third reaction effluent as by-product may be reacted with methanol or ethanol and with oxygen in an additional reactor to form methyl or ethyl nitrite, which is then recycled to the coupling reactor to be used.

Without being limited to a theory, it is believed that 1) the oxalate product formed by coupling of CO in the presence of a nitrite could further undergo secondary reaction when it passes through a later catalyst bed layer, thereby reducing the selectivity to the target product, and 2) the presence of the oxalate product could kinetically inhibit the conversion of the feedstock or reduce the activity of the catalyst, thereby resulting in the decrease of the single-pass conversion of the feedstock and increase of the circulating amount. The first process described herein employs at least two reaction zones in series, with the effluent of a preceding reaction zone being subjected to gas-liquid separation in a gas-liquid separator, the liquid phase stream as a crude product being passed into a separation unit to obtain the target product, and the gas phase stream being fed to the next reaction zone. Such an arrangement could not only reduce the probability of secondary reaction of the target product but also be kinetically favor of accelerating the rate of the main reaction, thereby achieving the purpose of enhancing the selectivity to the target product and the single-pass conversion of the feedstock.

Additionally, the reaction of coupling CO into an oxalate is an exothermal reaction. It is believed that a main cause deactivating a catalyst used in the reaction of coupling CO into an oxalate could be the sintering of the grains of the catalytic active component. Concentrative exotherm during the coupling reaction may result in a higher temperature rise in the catalyst, for example, on the catalytic active sites, of which temperature may be higher than the apparent temperature of the catalyst by tens or even more than one hundred degrees Celsius. Over high local temperature rise could seriously influence the lifetime of the catalyst, because it could greatly accelerate the growth of the grains, thereby accelerating the deactivation of the catalyst. The first process described herein uses at least two reaction zones in series, and the effluent from the preceding reaction zone(s) is subjected to a phase separation in a gas-liquid separator, so that the temperature profile during the reaction may be optimized.

In some embodiments, the first process described herein comprises: feeding CO and a nitrite to a first reaction zone to contact them with a first palladium-containing catalyst, to form a first reaction effluent, with the first reaction zone being operated under the following conditions: a reaction temperature ranging from 70 to 120° C., a reaction contacting time ranging from 0.7 to 5 seconds, and a reaction pressure ranging from 0.08 to 1.0 MPa; feeding the first reaction effluent to a gas-liquid separator, to obtain via gas-liquid separation a liquid product stream and a gas mixture stream; feeding the liquid product stream to a separation unit, to separate a first portion of the oxalate product; feeding the gas mixture stream to a second reaction zone to contact it with a second palladium-containing catalyst, to form a second reaction effluent containing the oxalate, with the second reaction zone being operated under the following conditions: a reaction temperature ranging from 80 to 140° C., a reaction contacting time ranging from 0.7 to 5 seconds, and a reaction pressure ranging from 0.08 to 1.0 MPa; feeding the second reaction effluent to the separation unit, to separate a second portion of the oxalate product, wherein the molar ratio of the raw material CO to the nitrite in the first reaction zone ranges, for example, from 1:1 to 3:1, wherein the first palladium-containing catalyst and the second palladium-containing catalyst comprise, for example, alumina as carrier, and palladium as active component in an amount ranging, for example, from 0.2 to 3 wt % based on the weight of the carrier. In some embodiments, a single-pass conversion of CO of up to more than 71% and a selectivity to the oxalate of up to more than 99% may be achieved.

Also provided is a process for producing an oxalate by coupling of CO (referred to as the second process), comprising a) feeding a first nitrite stream and CO feedstock to a first reaction zone to contact them with a first palladium-containing catalyst, to form a first reaction effluent containing the oxalate;

b) optionally, passing the first reaction effluent into a gas-liquid separator to conduct gas-liquid separation, to obtain a gas stream and a liquid product stream, with the liquid product stream being passed into a separation unit to separate the oxalate product;

c) feeding the first reaction effluent or the gas stream obtained from b) together with a second nitrite stream to a second reaction zone to contact them with a second palladium-containing catalyst, to form a second reaction effluent containing the oxalate; and d) passing the second reaction effluent into a separation unit to separate the oxalate product, wherein the molar ratio of the nitrite in the first nitrite stream to the nitrite in the second nitrite stream ranges, for example, from 0.1:1 to 10:1, and wherein the molar ratio of the CO to the total nitrite in the first nitrite stream and the second nitrite stream ranges, for example, from 1:1 to 5:1, such as from 1:1 to 3:1.

In some embodiments of the second process, the first reaction zone is operated at a reaction temperature ranging from 60 to 150° C., such as from 70 to 140° C. In some embodiments of the second process, the first reaction zone is operated at a reaction contacting time ranging from 0.5 to 6 seconds, such as from 0.7 to 5 seconds. In some embodiments of the second process, the first reaction zone is operated at a reaction pressure ranging from 0.05 to 1.5 MPa, such as from 0.08 to 1.0 MPa. In some embodiments of the second process, the first reaction zone is operated under the following conditions: a reaction temperature ranging from 60 to 150° C., such as from 70 to 140° C.; a reaction contacting time ranging from 0.5 to 6 seconds, such as from 0.7 to 5 seconds; and a reaction pressure ranging from 0.05 to 1.5 MPa, such as from 0.08 to 1.0 MPa.

In some embodiments of the second process, the second reaction zone is operated at a reaction temperature ranging from 70 to 160° C., such as from 80 to 150° C. In some embodiments of the second process, the second reaction zone is operated at a reaction contacting time ranging from 0.5 to 6 seconds, such as from 0.7 to 5 seconds. In some embodiments of the second process, the second reaction zone is operated at a reaction pressure ranging from 0.05 to 1.5 MPa, such as from 0.08 to 1.0 MPa. In some embodiments of the second process, the second reaction zone is operated under the following conditions: a reaction temperature ranging from 70 to 160° C., such as from 80 to 150° C.; a reaction contacting time ranging from 0.5 to 6 seconds, such as from 0.7 to 5 seconds; and a reaction pressure ranging from 0.05 to 1.5 MPa, such as from 0.08 to 1.0 MPa.

In some embodiments of the second process, the molar ratio of the nitrite in the first nitrite stream to the nitrite in the second nitrite stream ranges, for example, from 0.1:1 to 10:1, such as from 0.2:1 to 8:1, further such as from 0.4:1 to 6:1.

The palladium-containing catalysts that can be used in the second process are as described for the first process.

The nitrites that can be used in the second process include, for example, methyl nitrite and ethyl nitrite. NO separated from the second reaction effluent as a by-product of the reaction may react with methanol or ethanol as well as oxygen in an additional reactor to form methyl nitrite or ethyl nitrite, which can be recycled to the coupling reactor.

It will be understood by those skilled in the art that, in the case where the second reaction effluent still comprises a relatively large quantity of unreacted CO, the second process may further comprise the use of a third reaction zone, wherein the second reaction effluent or a CO-containing gas stream separated from the second reaction effluent together with a third nitrite stream are fed to the third reaction zone to contact with a third palladium-containing catalyst, to form a third reaction effluent containing the oxalate, from which the oxalate product could be separated. The catalyst and operation conditions employed in the third reaction zone are similar to those as described for the second reaction zone.

Generally, the second process employs at least two reaction zones in series, a nitrite being introduced stagewise, and the oxalate product being optionally separated between the reaction zones. As indicated above, it is believed that a main cause deactivating a catalyst used in the reaction of coupling CO into an oxalate is the sintering of the grains of the catalytic active component. Concentrative exotherm during the coupling reaction may result in a higher temperature rise in the catalyst, such as on the catalytic active sites, of which temperature may be higher than the apparent temperature of the catalyst by tens or even more than one hundred degrees Celsius. Over high local temperature rise could seriously influence the lifetime of the catalyst, because it greatly accelerates the growth of the grains, thereby accelerating the deactivation of the catalyst. The stagewise addition of the nitrite and the optional separation of the oxalate product between the reaction zones could help to optimize the temperature profile during the reaction. It is also believed that, during the coupling reaction of CO in the presence of a nitrite to form an oxalate, the heat decomposition of the nitrite is a main cause resulting in the decrease of the yield of and the selectivity to the oxalate as target product, while the probability of the heat decomposition of the nitrite could be closely correlated to the concentration of the nitrite. Thus, the stagewise addition of the nitrite could reduce advantageously the probability of nitrite decomposition, and help enhance the selectivity to and the yield of the target product. Furthermore, the separation of the oxalate product between the reaction zones may avoid the secondary reaction undergone by the oxalate product when it passes through the later reaction zone(s), so that the selectivity to the target product and the single-pass conversion of CO can be enhanced.

In some embodiments, the second process comprises: feeding CO and a first nitrite stream to a first reaction zone to contact them with a first palladium-containing catalyst, to form a first reaction effluent containing an oxalate, with the first reaction zone being operated under the following conditions: a reaction temperature ranging from 70 to 140° C., a reaction contacting time ranging from 0.7 to 5 seconds, and a reaction pressure ranging from 0.08 to 1.0 MPa; optionally, passing the first reaction effluent into a gas-liquid separator, to obtain via gas-liquid separation a gas stream and a liquid product stream, which liquid product stream is passed to a separation unit to separate the oxalate product; feeding the first reaction effluent or the gas stream from the gas-liquid separator, together with a second nitrite stream, to a second reaction zone to contact it with a second palladium-containing catalyst, to form a second reaction effluent containing the oxalate, with the second reaction zone being operated under the following conditions: a reaction temperature ranging from 80 to 150° C., a reaction contacting time ranging from 0.7 to 5 seconds, and a reaction pressure ranging from 0.08 to 1.0 MPa; and passing the second reaction effluent into a separation unit to separate the oxalate product, wherein the molar ratio of the nitrite in the first nitrite stream to the nitrite in the second nitrite stream ranges, for example, from 0.4:1 to 6:1, wherein the molar ratio of the CO to the total nitrite in the first nitrite stream and the second nitrite stream ranges, for example, from 1:1 to 3:1, and wherein both the first and the second palladium-containing catalysts comprise, for example, alumina as carrier, and palladium as active component in an amount ranging, for example, from 0.2 to 3 wt % based on the weight of the carrier. In some embodiments, a single-pass conversion of CO of up to more than 70%, and a selectivity to the oxalate of up to more than 99% is achieved.

The following examples are given for further illustrating the disclosure, but do not make limitation to the disclosure in any way.

General Procedure for Preparing Catalysts

The palladium catalysts used in the following examples were prepared as follows:

An amount of palladium nitrate was dissolved in water, and the solution was adjusted with nitric acid or hydrochloric acid to a pH value ranging from 3 to 6. The solution was heated to 60 to 80° C., and then an amount of a support, e.g., pellets of alumina, was impregnated with the solution for a period ranging from 8 to 24 hours. The impregnated support was dried at a temperature ranging from 110 to 130° C. for a period of time ranging from 4 to 8 hrs, and then calcined in air at a temperature ranging from 300 to 450° C. for a period of time ranging from 4 to 8 hrs, followed by the reduction with hydrogen at 300° C. for 4 hrs, to obtain the desired palladium catalyst.

EXAMPLE 1

Palladium catalyst comprising alumina as carrier and palladium in an amount of 1.5 wt % based on the weight of the carrier was prepared according to the above-described method. The palladium catalyst was loaded in a first reactor and a second reactor. A mixture of CO and methyl nitrite (the molar ratio of the CO to the methyl nitrite was 1.2:1) was fed to the first reactor to contact with the palladium catalyst contained therein, to form a first reaction effluent. The first reaction effluent was fed to a gas-liquid separator, to obtain via gas-liquid separation a liquid product stream and a gas mixture stream. The liquid product stream was passed into a separation unit to obtain via separation dimethyl oxalate product. The gas mixture stream was fed to the second reactor to contact with the palladium catalyst contained therein, to form a second reaction effluent. The second reaction effluent was passed into the separation unit to obtain, via separation, additional dimethyl oxalate product. The first reactor was operated under the following conditions: a reaction temperature of 90° C., a reaction contacting time of 1 second, and a reaction pressure of 0.08 MPa; and the second reactor was operated under the following conditions: a reaction temperature of 130° C., a reaction contacting time of 3 seconds, and a reaction pressure of 0.08 MPa. Reaction results were found as follows: the CO single-pass conversion was 62.3%, and the selectivity to dimethyl oxalate was 97.2%.

EXAMPLE 2

A palladium catalyst I and a palladium catalyst II were prepared according to the above-described method, wherein the palladium catalyst I comprised silica as carrier and palladium in an amount of 0.5 wt % based on the carrier, and the palladium catalyst II comprised alumina as carrier and palladium in an amount of 1 wt % based on the carrier. The palladium catalyst I and palladium catalyst II were loaded in a first reactor and a second reactor, respectively. A mixture of CO and methyl nitrite (the molar ratio of the CO to the methyl nitrite was 1.5:1) was fed to the first reactor to contact with the palladium catalyst I, to form a first reaction effluent. The first reaction effluent was fed to a gas-liquid separator, to obtain via gas-liquid separation a liquid product stream and a gas mixture stream. The liquid product stream was passed into a separation unit to obtain via separation a dimethyl oxalate product. The gas mixture stream was fed to a second reactor to contact with the palladium catalyst II, to form a second reaction effluent. The second reaction effluent was passed into the separation unit to obtain after separating additional dimethyl oxalate product. The first reactor was operated under the following conditions: a reaction temperature of 100° C., a reaction contacting time of 1 second, and a reaction pressure of 0.15 MPa; and the second reactor was operated under the following conditions: a reaction temperature of 150° C., a reaction contacting time of 3 seconds, and a reaction pressure of 0.15 MPa. Reaction results were found as follows: the CO single-pass conversion was 55.4%, and the selectivity to dimethyl oxalate was 97.9%.

EXAMPLE 3

A palladium catalyst I and a palladium catalyst II were prepared according to the above-described method, wherein the palladium catalyst I comprises ZSM-5 molecular sieve having a Si/Al molar ratio of 150:1 as carrier, and palladium in an amount of 0.6 wt % based on the carrier, and the palladium catalyst II comprises alumina as carrier, and palladium in an amount of 3 wt % based on the carrier. The palladium catalyst I and the palladium catalyst II were loaded in a first reactor and a second reactor, respectively. A mixture of CO and ethyl nitrite (the molar ratio of the CO to the ethyl nitrite was 1:1) was fed to the first reactor to contact with the palladium catalyst I, to form a first reaction effluent. The first reaction effluent was fed to a gas-liquid separator, to obtain via gas-liquid separation a liquid product stream and a gas mixture stream. The liquid product stream was passed into a separation unit to obtain after separating a diethyl oxalate product. The gas mixture stream was fed to the second reactor to contact with the palladium catalyst II, to form a second reaction effluent. The second reaction effluent was passed into the separation unit to obtain after separating additional diethyl oxalate product. The first reactor was operated under the following conditions: a reaction temperature of 80° C., a reaction contacting time of 3 seconds, and a reaction pressure of 1.5 MPa; and the second reactor was operated under the following conditions: a reaction temperature of 120° C., a reaction contacting time of 4 seconds, and a reaction pressure of 1.5 MPa. Reaction results were found as follows: the CO single-pass conversion was 66.4%, and the selectivity to diethyl oxalate was 98.1%.

EXAMPLE 4

A palladium catalyst I and a palladium catalyst II were prepared according to the above-described method, wherein the palladium catalyst I and the palladium catalyst II comprised alumina as carrier, and palladium in an amount of 0.8 wt % and 1.2 wt % based on the carrier, respectively. The palladium catalyst I and the palladium catalyst II were loaded in a first reactor and a second reactor, respectively. A mixture of CO and ethyl nitrite (the molar ratio of the CO to the ethyl nitrite was 1.6:1) was fed to the first reactor to contact with the palladium catalyst I, to form a first reaction effluent. The first reaction effluent was fed to a gas-liquid separator, to obtain via gas-liquid separation a liquid product stream and a gas mixture stream. The liquid product stream was passed into a separation unit to obtain after separating a diethyl oxalate product. The gas mixture stream was fed to the second reactor to contact with the palladium catalyst II, to form a second reaction effluent. The second reaction effluent was passed into the separation unit to obtain after separating additional diethyl oxalate product. The first reactor was operated under the following conditions: a reaction temperature of 95° C., a reaction contacting time of 1 second, and a reaction pressure of 0.5 MPa; and the second reactor was operated under the following conditions: a reaction temperature of 110° C., a reaction contacting time of 4 seconds, and a reaction pressure of 0.5 MPa. Reaction results were found as follows: CO single-pass conversion was 45.4%, and the selectivity to diethyl oxalate was 98.8%.

EXAMPLE 5

A palladium catalyst I and a palladium catalyst II were prepared according to the above-described method, wherein the palladium catalyst I and the palladium catalyst II comprised alumina as carrier, and palladium in an amount of 0.4 wt % and 5 wt % based on the carrier, respectively. The palladium catalyst I and the palladium catalyst II were loaded in a first reactor and a second reactor, respectively. A mixture of CO and ethyl nitrite (the molar ratio of the CO to the ethyl nitrite was 2:1) was fed to the first reactor to contact with the palladium catalyst I, to form a first reaction effluent. The first reaction effluent was fed to a gas-liquid separator, to obtain via gas-liquid separation a liquid product stream and a gas mixture stream. The liquid product stream was passed into a separation unit to obtain after separating a diethyl oxalate product. The gas mixture stream was fed to the second reactor to contact with the palladium catalyst II, to form a second reaction effluent. The second reaction effluent was passed into the separation unit to obtain after separating additional diethyl oxalate product. The first reactor was operated under the following conditions: a reaction temperature of 95° C., a reaction contacting time of 2 seconds, and a reaction pressure of 0.5 MPa; and the second reactor was operated under the following conditions: a reaction temperature of 110° C., a reaction contacting time of 0.5 seconds, and a reaction pressure of 0.5 MPa. Reaction results were found as follows: CO single-pass conversion was 44.4%, and the selectivity to diethyl oxalate was 99.3%.

EXAMPLE 6

A palladium catalyst I and a palladium catalyst II were prepared according to the above-described method, wherein the palladium catalyst I comprised MCM-22 as carrier, and palladium in an amount of 3 wt % based on the carrier, and the palladium catalyst II comprised β zeolite as carrier, and palladium in an amount of 2 wt % based on the carrier. The palladium catalyst I and the palladium catalyst II were loaded in a first reactor and a second reactor, respectively. A mixture of CO and ethyl nitrite (the molar ratio of the CO to the ethyl nitrite was 3:1) was fed to the first reactor to contact with the palladium catalyst I, to form a first reaction effluent. The first reaction effluent was fed to a gas-liquid separator, to obtain via gas-liquid separation a liquid product stream and a gas mixture stream. The liquid product stream was passed into a separation unit to obtain after separating a diethyl oxalate product. The gas mixture stream was fed to the second reactor to contact with the palladium catalyst II, to form a second reaction effluent. The second reaction effluent was passed into the separation unit to obtain after separating additional diethyl oxalate product. The first reactor was operated under the following conditions: a reaction temperature of 80° C., a reaction contacting time of 3 seconds, and a reaction pressure of 1.5 MPa; and the second reactor was operated under the following conditions: a reaction temperature of 120° C., a reaction contacting time of 4 seconds, and a reaction pressure of 1.5 MPa. Reaction results were found as follows: CO single-pass conversion was 25.2%, and the selectivity to diethyl oxalate was 99.2%.

EXAMPLE 7

A palladium catalyst was prepared according to the above-described method, wherein the palladium catalyst comprised alumina as carrier, and palladium in an amount of 1.5 wt % based on the carrier. The palladium catalyst was loaded in a first reactor, a second reactor and a third reactor. A mixture of CO and methyl nitrite (the molar ratio of the CO to the methyl nitrite was 1:1) was fed to the first reactor to contact with the palladium catalyst contained therein, to form a first reaction effluent. The first reaction effluent was fed to a first gas-liquid separator, to obtain via gas-liquid separation a first liquid product stream and a first gas mixture stream. The first liquid product stream was passed into a separation unit to obtain after separating a first portion of dimethyl oxalate product. The first gas mixture stream was fed to the second reactor to contact with the palladium catalyst contained therein, to form a second reaction effluent. The second reaction effluent was passed into a second gas-liquid separator, to obtain via gas-liquid separation a second liquid product stream and a second gas mixture stream. The second liquid product stream was passed into the separation unit to obtain after separating a second portion of dimethyl oxalate product. The second gas mixture stream was fed to the third reactor to contact with the palladium catalyst contained therein, to form a third reaction effluent. The third reaction effluent was passed into the separation unit to obtain after separating a third portion of dimethyl oxalate product. The first reactor was operated under the following conditions: a reaction temperature of 130° C., a reaction contacting time of 1 second, and a reaction pressure of 0.08 MPa; and both the second and the third reactor were operated under the following conditions: a reaction temperature of 130° C., a reaction contacting time of 3 seconds, and a reaction pressure of 0.08 MPa. Reaction results were found as follows: CO single-pass conversion was 75.2%, and selectivity to dimethyl oxalate was 98.9%.

COMPARATIVE EXAMPLE 1

This experiment was performed in only one reactor by using the same catalyst, conditions and feedstock as used in the first reactor in Example 7, except that the contacting time was 6.5 seconds. Reaction results were found as follows: CO single-pass conversion was 55.3%, and selectivity to dimethyl oxalate was 94.1%.

EXAMPLE 8

This example used CO and methyl nitrite as feedstock, wherein the methyl nitrite was split into a first methyl nitrite stream and a second methyl nitrite stream, wherein the molar ratio of the CO to the total methyl nitrite was 1.2:1, and the molar ratio of the first methyl nitrite stream to the second methyl nitrite stream was 0.5:1.

A palladium catalyst comprising alumina as carrier and palladium in an amount of 0.5 wt % based on the carrier was prepared according to the above-described method. The palladium catalyst was loaded in a first reactor and a second reactor. The CO and the first methyl nitrite stream were fed to the first reactor to contact with the palladium catalyst contained therein, to form a first reaction effluent. The first reaction effluent and the second methyl nitrite stream were fed to the second reactor to contact with the palladium catalyst contained therein, to form a second reaction effluent. Dimethyl oxalate product was separated from the second reaction effluent. The first reactor was operated under the following conditions: a reaction temperature of 110° C., a reaction contacting time of 0.5 seconds, and a reaction pressure of 0.08 MPa; and the second reactor was operated under the following conditions: a reaction temperature of 140° C., a reaction contacting time of 3 seconds, and a reaction pressure of 0.08 MPa. Reaction results were found as follows: CO single-pass conversion was 65.8%, and selectivity to dimethyl oxalate was 97.8%.

EXAMPLE 9

This example used CO and methyl nitrite as feedstock, wherein the methyl nitrite was split into a first methyl nitrite stream and a second methyl nitrite stream, wherein the molar ratio of the CO to the total methyl nitrite was 1.5:1, and the molar ratio of the first methyl nitrite stream to the second methyl nitrite stream was 3:1.

A palladium catalyst I and a palladium catalyst II were prepared according to the above-described method, wherein the palladium catalyst I comprised silica as carrier and palladium in an amount of 1.5 wt % based on the carrier, and the palladium catalyst II comprised alumina as carrier and palladium in an amount of 1 wt % based on the carrier. The palladium catalyst I and the palladium catalyst II were loaded in a first reactor and a second reactor, respectively. The CO and the first methyl nitrite stream were fed to the first reactor to contact with the palladium catalyst I, to form a first reaction effluent. The first reaction effluent and the second methyl nitrite stream were fed to the second reactor to contact with the palladium catalyst II, to form a second reaction effluent. Dimethyl oxalate product was separated from the second reaction effluent. The first reactor was operated under the following conditions: a reaction temperature of 100° C., a reaction contacting time of 1 second, and a reaction pressure of 0.15 MPa; and the second reactor was operated under the following conditions: a reaction temperature of 150° C., a reaction contacting time of 4 seconds, and a reaction pressure of 0.15 MPa. Reaction results were found as follows: CO single-pass conversion was 50.6%, and selectivity to dimethyl oxalate was 98.9%.

EXAMPLE 10

This example used CO and ethyl nitrite as feedstock, wherein the ethyl nitrite was split into a first ethyl nitrite stream and a second ethyl nitrite stream, wherein the molar ratio of the CO to the total ethyl nitrite was 1:1, and the molar ratio of the first ethyl nitrite stream to the second ethyl nitrite stream was 5:1.

A palladium catalyst I and a palladium catalyst II were prepared according to the above-described method, wherein the palladium catalyst I comprised a ZSM-5 molecular sieve having a Si/Al molar ratio of 300:1 as carrier and palladium in an amount of 0.6 wt % based on the carrier, and the palladium catalyst II comprised alumina as carrier and palladium in an amount of 3 wt % based on the carrier. The palladium catalyst I and a palladium catalyst II were loaded in a first reactor and a second reactor, respectively. The CO and the first ethyl nitrite stream were fed to the first reactor to contact with the palladium catalyst I, to form a first reaction effluent. The first reaction effluent and the second ethyl nitrite stream were fed to the second reactor to contact with the palladium catalyst II, to form a second reaction effluent. Diethyl oxalate product was separated from the second reaction effluent. The first reactor was operated under the following conditions: a reaction temperature of 80° C., a reaction contacting time of 3 seconds, and a reaction pressure of 1.5 MPa; and the second reactor was operated under the following conditions: a reaction temperature of 120° C., a reaction contacting time of 4 seconds, and a reaction pressure of 1.5 MPa. Reaction results were found as follows: CO single-pass conversion was 65.3%, and selectivity to diethyl oxalate was 98.3%.

EXAMPLE 11

This example used CO and ethyl nitrite as feedstock, wherein the ethyl nitrite was split into a first ethyl nitrite stream and a second ethyl nitrite stream, wherein the molar ratio of the CO to the total ethyl nitrite was 1.4:1, and the molar ratio of the first ethyl nitrite stream to the second ethyl nitrite stream was 8:1.

A palladium catalyst I and a palladium catalyst II were prepared according to the above-described method, wherein the palladium catalyst I and palladium catalyst II comprised alumina as carrier, and palladium in an amount of 2.5 wt % and 1.2 wt %, respectively, based on the carrier. The palladium catalyst I and the palladium catalyst II were loaded in a first reactor and a second reactor, respectively. The CO and the first ethyl nitrite stream were fed to the first reactor to contact with the palladium catalyst I, to form a first reaction effluent. The first reaction effluent and the second ethyl nitrite stream were fed to the second reactor to contact with the palladium catalyst II, to form a second reaction effluent. Diethyl oxalate product was separated from the second reaction effluent. The first reactor was operated under the following conditions: a reaction temperature of 95° C., a reaction contacting time of 2 seconds, and a reaction pressure of 0.5 MPa; and the second reactor was operated under the following conditions: a reaction temperature of 110° C., a reaction contacting time of 4 seconds, and a reaction pressure of 0.5 MPa. Reaction results were found as follows: CO single-pass conversion was 58.3%, and selectivity to diethyl oxalate was 98.3%.

EXAMPLE 12

This example used CO and ethyl nitrite as feedstock, wherein the ethyl nitrite was split into a first ethyl nitrite stream and a second ethyl nitrite stream, wherein the molar ratio of the CO to the total ethyl nitrite was 1:1, and the molar ratio of the first ethyl nitrite stream to the second ethyl nitrite stream was 5:1.

A palladium catalyst I and a palladium catalyst II were prepared according to the above-described method, wherein the palladium catalyst I and the palladium catalyst II comprised silica as carrier, and palladium in an amount of 0.4 wt % and 1.8 wt %, respectively, based on the carrier. The palladium catalyst I and the palladium catalyst II were loaded in a first reactor and a second reactor, respectively. The CO and the first ethyl nitrite stream were fed to the first reactor to contact with the palladium catalyst I, to form a first reaction effluent. The first reaction effluent and the second ethyl nitrite stream were fed to the second reactor to contact with the palladium catalyst II, to form a second reaction effluent. Diethyl oxalate product was separated from the second reaction effluent. The first reactor was operated under the following conditions: a reaction temperature of 120° C., a reaction contacting time of 2 seconds, and a reaction pressure of 0.5 MPa; and the second reactor was operated under the following conditions: a reaction temperature of 120° C., a reaction contacting time of 5 seconds, and a reaction pressure of 0.5 MPa. Reaction results were found as follows: CO single-pass conversion was 70.3%, and selectivity to diethyl oxalate was 98.9%.

EXAMPLE 13

This example used CO and ethyl nitrite as feedstock, wherein the ethyl nitrite was split into a first ethyl nitrite stream and a second ethyl nitrite stream, wherein the molar ratio of the CO to the total ethyl nitrite was 1:1, and the molar ratio of the first ethyl nitrite stream to the second ethyl nitrite stream was 5:1.

A palladium catalyst I and a palladium catalyst II were prepared according to the above-described method, wherein the palladium catalyst I comprised a ZSM-5 molecular sieve having a Si/Al molar ratio of 100:1 as carrier and palladium in an amount of 0.6 wt % based on the carrier, and the palladium catalyst II comprised silica as carrier and palladium in an amount of 3.0 wt % based on the carrier. The palladium catalyst I and the palladium catalyst II were loaded in a first reactor and a second reactor, respectively. The CO and the first ethyl nitrite stream were fed to the first reactor to contact with the palladium catalyst I, to form a first reaction effluent. The first reaction effluent and the second ethyl nitrite stream were fed to the second reactor to contact with the palladium catalyst II, to form a second reaction effluent. Diethyl oxalate product was separated from the second reaction effluent. The first reactor was operated under the following conditions: a reaction temperature of 140° C., a reaction contacting time of 4 seconds, and a reaction pressure of 1.5 MPa; and the second reactor was operated under the following conditions: a reaction temperature of 120° C., a reaction contacting time of 4 seconds, and a reaction pressure of 1.5 MPa. Reaction results were found as follows: CO single-pass conversion was 73.3%, and selectivity to diethyl oxalate was 99.1%.

EXAMPLE 14

This example used CO and methyl nitrite as feedstock, wherein the methyl nitrite was split into a first methyl nitrite stream and a second methyl nitrite stream, wherein the molar ratio of the CO to the total methyl nitrite was 1.2:1, and the molar ratio of the first methyl nitrite stream to the second methyl nitrite stream was 0.5:1.

A palladium catalyst I and a palladium catalyst II were prepared according to the above-described method, wherein the palladium catalyst I and the palladium catalyst II comprised alumina as carrier, and palladium in an amount of 1.0 wt % and 1.2 wt %, respectively, based on the carrier. The palladium catalyst I and the palladium catalyst II were loaded in a first reactor and a second reactor, respectively. The CO and the first methyl nitrite stream were fed to the first reactor to contact with the palladium catalyst I, to form a first reaction effluent. The first reaction effluent and the second methyl nitrite stream were fed to the second reactor to contact with the palladium catalyst II, to form a second reaction effluent. Dimethyl oxalate product was separated from the second reaction effluent. The first reactor was operated under the following conditions: a reaction temperature of 160° C., a reaction contacting time of 3 seconds, and a reaction pressure of 0.08 MPa; and the second reactor was operated under the following conditions: a reaction temperature of 130° C., a reaction contacting time of 3 seconds, and a reaction pressure of 0.08 MPa. Reaction results were found as follows: CO single-pass conversion was 60.8%, and selectivity to dimethyl oxalate was 99.1%.

COMPARATIVE EXAMPLE 2

This experiment was performed in only one reactor by using the same catalyst, conditions and feedstock as used in the first reactor in Example 14, except that the contacting time was 5 seconds. Reaction results were found as follows: CO single-pass conversion was 48.3%, and selectivity to dimethyl oxalate was 93.0%.

EXAMPLE 15

This example used CO and methyl nitrite as feedstock, wherein the methyl nitrite was split into a first methyl nitrite stream and a second methyl nitrite stream, wherein the molar ratio of the CO to the total methyl nitrite was 1.5:1, and the molar ratio of the first methyl nitrite stream to the second methyl nitrite stream was 3:1.

A palladium catalyst I and a palladium catalyst II were prepared according to the above-described method, wherein the palladium catalyst I comprised silica as carrier and palladium in an amount of 1.5 wt % based on the carrier, and the palladium catalyst II comprised alumina as carrier and palladium in an amount of 1.0 wt % based on the carrier. The palladium catalyst I and the palladium catalyst II were loaded in a first reactor and a second reactor, respectively. The CO and the first methyl nitrite stream were fed to the first reactor to contact with the palladium catalyst I, to form a first reaction effluent. The first reaction effluent was passed into a gas-liquid separator, to obtain via gas-liquid separation a liquid product stream and a gas mixture stream. The liquid product stream was passed into a separation unit to obtain after separating dimethyl oxalate product. The gas mixture stream and the second methyl nitrite stream were fed to the second reactor to contact with the palladium catalyst II, to form a second reaction effluent. The second reaction effluent was passed into the separation unit to obtain after separating additional dimethyl oxalate product. The first reactor was operated under the following conditions: a reaction temperature of 100° C., a reaction contacting time of 1 second, and a reaction pressure of 0.15 MPa; and the second reactor was operated under the following conditions: a reaction temperature of 150° C., a reaction contacting time of 4 seconds, and a reaction pressure of 0.15 MPa. Reaction results were found as follows: CO single-pass conversion was 63.6%, and selectivity to dimethyl oxalate was 99.5%.

While the disclosure has been described with reference to exemplary embodiments, it will be understood by those skilled in the art that various changes and modifications may be made without departing from the spirit and scope of the disclosure. Therefore, the disclosure is not limited to the embodiments disclosed herein, but the disclosure includes all embodiments falling within the scope of the appended claims.

What is claimed is:

1. A process for producing an oxalate by coupling of CO, comprising
   a) feeding a nitrite and CO as feedstock to a first reaction zone to contact them with a first palladium-containing catalyst, to form a first reaction effluent containing unreacted nitrite, CO and oxalate product;
   b) passing the first reaction effluent into a gas-liquid separator to conduct gas-liquid separation, to obtain a liquid product stream and a gas mixture stream;
   c) feeding the liquid product stream obtained from b) to a separation unit, to obtain a first portion of the oxalate product;
   d) feeding the gas mixture stream obtained from b) to a second reaction zone to contact it with a second palladium-containing catalyst, to form a second reaction effluent containing the oxalate; and
   e) feeding the second reaction effluent to the separation unit, to obtain a second portion of the oxalate product, wherein the molar ratio of the CO to the nitrite in the feedstock fed to the first reaction zone is from 1:1 to 5:1.

2. The process of claim 1, wherein the first reaction zone is operated under the following conditions: a reaction temperature ranging from 60 to 130° C., a reaction contacting time ranging from 0.5 to 6 seconds, and a reaction pressure ranging from 0.05 to 1.5 MPa; and the second reaction zone is operated under the following conditions: a reaction temperature ranging from 70 to 150° C., a reaction contacting time ranging from 0.5 to 6 seconds, and a reaction pressure ranging from 0.05 to 1.5 MPa.

3. The process of claim 2, wherein the first reaction zone is operated under the following conditions: a reaction temperature ranging from 70 to 120° C., a reaction contacting time ranging from 0.7 to 5 seconds, and a reaction pressure ranging from 0.08 to 1.0 MPa; and the second reaction zone is operated under the following conditions: a reaction temperature ranging from 80 to 140° C., a reaction contacting time ranging from 0.7 to 5 seconds, and a reaction pressure ranging from 0.08 to 1.0 MPa.

4. The process of claim 1, wherein the first palladium-containing catalyst and the second palladium-containing catalyst are the same or different, employ at least one carrier selected from silica, alumina and molecular sieves, and comprise from 0.1 to 5 wt % of palladium as active component, based on the carrier.

5. The process of claim 4, wherein the molecular sieves are chosen from ZSM-5, mordenite, MCM-22 and β zeolite.

6. The process of claim 4, wherein the first palladium-containing catalyst and the second palladium-containing catalyst are the same or different, employ alumina as carrier, and comprise from 0.2 to 3 wt % of palladium, based on the carrier.

7. The process of claim 1, wherein the nitrite is selected from methyl nitrite, ethyl nitrite, and mixtures thereof.

8. The process of claim 1, further comprising f): feeding a CO and nitrite-containing gas stream separated from the second reaction effluent to a third reaction zone to contact it with a third palladium-containing catalyst, to form a third reaction effluent containing the oxalate, from which a third portion of the oxalate product is separated.

9. The process of claim 1, further comprising g): reacting NO as a by-product of the reaction separated from the second reaction effluent with a corresponding alcohol and oxygen in an additional reactor, to form the nitrite, which is recycled to the coupling reactor.

10. The process of claim 8, further comprising g): reacting NO as a by-product of the reaction separated from the third reaction effluent with a corresponding alcohol and oxygen in an additional reactor, to form the nitrite, which is recycled to the coupling reactor.

11. A process for producing an oxalate by the coupling of CO, comprising
a) feeding a first nitrite stream and CO feedstock to a first reaction zone to contact them with a first palladium-containing catalyst, to form a first reaction effluent containing the oxalate;
b) optionally, passing the first reaction effluent into a gas-liquid separator to conduct gas-liquid separation, to obtain a gas stream and a liquid product stream, with the liquid product stream being passed into a separation unit to separate the oxalate product;
c) feeding the first reaction effluent or the gas stream obtained from b) together with a second nitrite stream to a second reaction zone to contact them with a second palladium-containing catalyst, to form a second reaction effluent containing the oxalate; and
d) passing the second reaction effluent into a separation unit to separate the oxalate product,
wherein the molar ratio of the nitrite in the first nitrite stream to the nitrite in the second nitrite stream ranges from 0.1:1 to 10:1, and wherein the molar ratio of the CO to the total nitrite in the first nitrite stream and the second nitrite stream ranges from 1:1 to 5:1.

12. The process of claim 11, wherein the first reaction zone is operated under the following conditions: a reaction temperature ranging from 60 to 150° C., a reaction contacting time ranging from 0.5 to 6 seconds, and a reaction pressure ranging from 0.05 to 1.5 MPa, wherein the second reaction zone is operated under the following conditions: a reaction temperature ranging from 70 to 160° C., a reaction contacting time ranging from 0.5 to 6 seconds, and a reaction pressure ranging from 0.05 to 1.5 MPa, and wherein the molar ratio of the nitrite in the first nitrite stream to the nitrite in the second nitrite stream ranges from 0.2:1 to 8:1.

13. The process of claim 12, wherein the first reaction zone is operated under the following conditions: a reaction temperature ranging from 70 to 140° C., a reaction contacting time ranging from 0.7 to 5 seconds, and a reaction pressure ranging from 0.08 to 1.0 MPa, wherein the second reaction zone is operated under the following conditions: a reaction temperature ranging from 80 to 150° C., a reaction contacting time ranging from 0.7 to 5 seconds, and a reaction pressure ranging from 0.08 to 1.0 MPa, and wherein the molar ratio of the nitrite in the first nitrite stream to the nitrite in the second nitrite stream ranges from 0.4:1 to 6:1.

14. The process of claim 11, wherein the first palladium-containing catalyst and the second palladium-containing catalyst are the same or different, employ at least one carrier selected from silica, alumina and molecular sieves, and comprise from 0.1 to 5 wt % of palladium as active component, based on the carrier.

15. The process of claim 14, wherein the molecular sieves are chosen from ZSM-5, mordenite, MCM-22 and β zeolite.

16. The process of claim 14, wherein the first palladium-containing catalyst and the second palladium-containing catalyst are the same or different, employ alumina as carrier, and comprise from 0.2 to 3 wt % of palladium, based on the carrier.

17. The process of claim 11, wherein the nitrite is selected from methyl nitrite, ethyl nitrite, and mixtures thereof.

18. The process of claim 11, wherein a CO-containing gas stream separated from the second reaction effluent in d) and a third nitrite stream are fed to a third reaction zone to contact with a third palladium-containing catalyst or, alternatively, d) is omitted and the second reaction effluent, together with a third nitrite stream, is directly fed to a third reaction zone to contact with a third palladium-containing catalyst, to form a third reaction effluent containing the oxalate, from which the oxalate product is separated.

19. The process of claim 11, further comprising e): reacting NO as a by-product of the reaction separated from the second reaction effluent with a corresponding alcohol and oxygen in an additional reactor, to form the nitrite, which is recycled to the coupling reactor.

20. The process of claim 18, further comprising e): reacting NO as a by-product of the reaction separated from the third reaction effluent with a corresponding alcohol and oxygen in an additional reactor, to form the nitrite, which is recycled to the coupling reactor.

* * * * *